(12) United States Patent
Cartledge et al.

(10) Patent No.: US 6,830,794 B2
(45) Date of Patent: *Dec. 14, 2004

(54) INSULATED INTRAVENOUS ADMINISTRATION TUBING

(76) Inventors: Richard G. Cartledge, 4271 Mangrum Ct., Hollywood, FL (US) 33021; Hugh F. Smisson, III, 4792 Brae Burn, Macon, GA (US) 31210

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 326 days.

(21) Appl. No.: 09/374,150

(22) Filed: Aug. 13, 1999

(65) Prior Publication Data

US 2002/0061375 A1 May 23, 2002

(51) Int. Cl.[7] .......................... B32B 1/08; B32B 27/08; B32B 27/30
(52) U.S. Cl. .................... 428/36.91; 138/137; 138/141; 138/178; 428/216; 428/220; 428/475; 604/264
(58) Field of Search .............................. 428/36.91, 216, 428/220, 475; 138/137, 141, 178; 604/264

(56) References Cited

U.S. PATENT DOCUMENTS

| | | | |
|---|---|---|---|
| 4,484,586 A | * 11/1984 | McMickle et al. | .......... 128/786 |
| 4,654,240 A | * 3/1987 | Johnston | ...................... 428/35 |
| 5,562,127 A | * 10/1996 | Fanselow et al. | ........... 138/137 |

FOREIGN PATENT DOCUMENTS

EP          0136848       * 4/1985

* cited by examiner

Primary Examiner—Sandra M. Nolan

(57) ABSTRACT

Insulated intravenous administration tubing is disclosed. One embodiment of the present invention includes a single medical solution or I.V. tubing manufactured of a polymeric material having good flexibility and comprising an insulation polymer or having an insulation medium applied to the inner or outer surface of the tube or blended into the tube during or after forming, with Mylar being an advantageous insulation material. The present invention may also consist of a long tubular-like structure which consists of two concentric channels, an inner channel and an outer channel. The inner channel accepts and encloses the tubing in which warm fluid flows. Three key functions are, achieved: the inner channel is centered within the outer channel; this provides for maximum insulation efficiency/properties with the minimum of separating space, transparency may be provided; i.e. the more transparent the insulation the better the ability of the user to see the quality of the warm fluid flowing within, i.e. detect air bubbles, ease of set-up and usability is provided. All components may be made of clear, flexible, light-weight materials to permit insulation and visualization of I.V. fluids and air bubbles. The insulated tubing has particular use, but not limited to, preventing convective heat loss of warmed I.V. fluid as it flows through the I.V. tubing, that would otherwise be exposed to ambient room temperature.

6 Claims, 1 Drawing Sheet

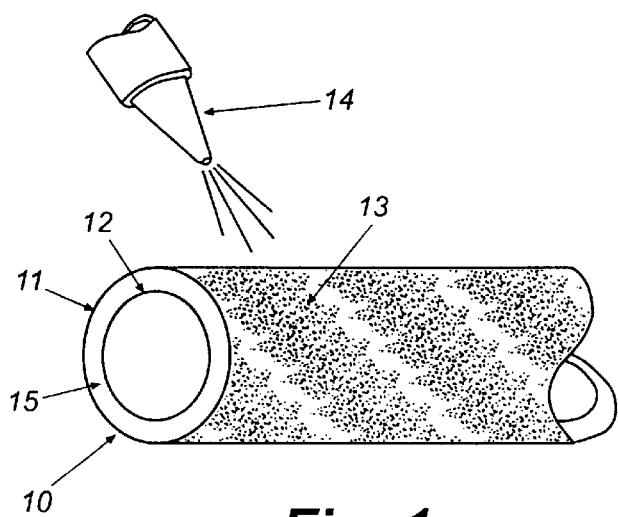
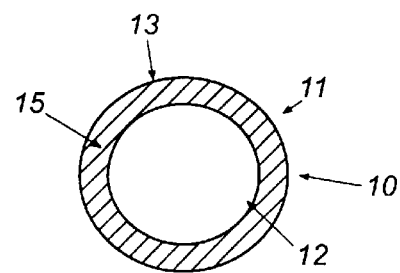
Fig. 1     Fig. 2
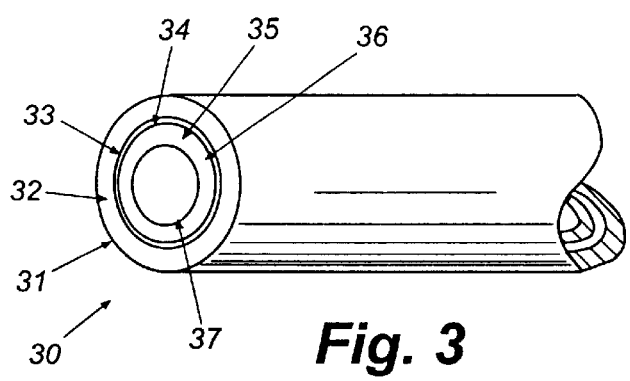
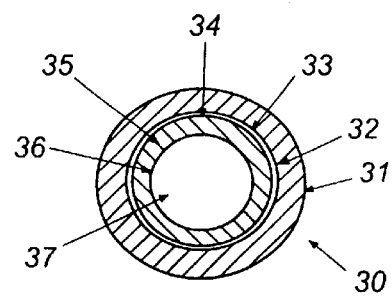
Fig. 3     Fig. 4

INSULATED INTRAVENOUS ADMINISTRATION TUBING

BACKGROUND OF THE INVENTION

Patients in hospitals or otherwise under medical care frequently require a continuous supply of fluid injected directly into the body, the most commonly known procedure being intravenous feeding. A hollow needle secured to the patient, usually at the hand or wrist area, is connected to a tube which carries a nutrient fluid mixture and perhaps other medicinal fluids from a supply container that is usually suspended on a stand, such that fluid flow into the patient is effected under the influence of gravity.

This invention relates to method and apparatus for insulating warmed intravenous fluid from ambient temperature losses to minimize and prevent a significant decrease in warmed I.V. fluid temperature as the I.V. fluid passes through the I.V. administration set and tubing to a patient.

Sterile fluids for intravenous (I.V.) administration into the human body often require warming from ambient temperature (20 degree C.) to approximate body temperature (37 degree C.) before or during their introduction. The purpose of warming I.V. fluids and chilled blood to approximately 37 degree C. is to improve the maintenance of body temperature. This is especially true during anesthesia and surgery when body temperature falls due to surgical exposure of large body surface areas to ambient temperature and interference of normal body thermo-regulatory mechanisms by anesthesia. This results in the patient becoming cool, often shivering post-operatively; patients may stay longer in the recovery room to recover from hypothermia.

Current technology to provide warm I.V. fluids to patients undergoing anesthesia and surgery are in-line fluid warmers and external fluid warmers. In-line fluid warmers heat I.V. fluid up to body temperature by applying heat directly (via an in-line heating element) to the I.V. fluid as it passes from the I.V. fluid reservoir (glass bottle or plastic bag) at ambient temperature to the patient. The in-line heating elements for in-line I.V. fluid warmers are disposable and costly per patient use.

External I.V. fluid warmers may be used to heat the I.V. fluid (in bulk) to 37 degree C. before administration to the patient. The external I.V. fluid heaters heat 6 to 20 separate I.V. fluid containers (plastic bags or glass bottles) simultaneously to approximately body temperature. The warmed I.V. bags are removed from the external heater as needed and placed into use, generally by hanging them from an I.V. pole and connecting to an administration set (which usually consist of drip chamber, I.V. tubing, roller clamps & connectors) and finally attaching to the patient's I.V. cannula. After hanging, the warmed I.V. fluid bags cool down approaching ambient temperature as time goes by, and further lose temperature as the warmed I.V. fluid passes through un-heated I.V. tubing and administration set at ambient temperature. Slower I.V. fluid flow rates result in cooler delivered I.V. fluids to the patient because the I.V. fluid cools down with time while passing through the interconnecting tubing of the administration set, exposed to ambient temperature, before entering the patient. This cooling effect with low I.V. fluid flow rates also affects any in-line fluid warmers during passage through the I.V. tubing from in-line warming device to patient.

Advantages exist in preventing heat loss of pre-warmed I.V. fluids during flow through I.V. administration tubing from an I.V. reservoir bag or bottle to the patient's anatomic administration site. The use of pre-warmed I.V. fluids are a practical, less expensive and more efficient method of administering warm I.V. fluids to patients as opposed to in-line I.V. fluid warmers. Compared to in-line I.V. fluid warmers, pre-warned I.V. fluids are: 1) less expensive, 2) less complicated to set up and administer, and 3) less bulky because of not requiring an active heating source to be placed near the patient.

It is an object of this invention to provide flexible insulated I.V. tubing from the I.V. reservoir bag or bottle to the patient anatomic administration site.

It is a further object of this invention to use a light-weight insulated I.V. tubing material to provide less bulk near the patient and optionally include the ability to visualize air bubbles in the I.V. tubing.

Other objects and advantages will become apparent in light of the attached drawings and description of the invention presented hereinbelow and the appended claims.

SUMMARY OF THE INVENTION

In accordance with one embodiment of the present invention, there is disclosed an insulated I.V. administration tubing.

Another embodiment of the invention provides a patient's I.V. administration tubing comprised of two flexible, optionally visually-clear or transparent, tube-like, concentric channels separated by an insulating space. This tubing includes an outer channel that forms an exterior covering. The outer channel optionally may be separated from the inner channel by an insulating space. The outer channel may also optionally provide a separation aligned with and attached to the inner channel by means of central support structures. Such an attachment of the inner and outer channel separations by means of the central support structures provides centering and maintains the inner channel within the outer channel.

Additional ancillary centering support structures may aid in keeping the inner channel centered and maintained within the outer channel when the course of the patient's I.V. tubing: 1) acutely bends 2) lays against other surfaces, or 3) is physically pressed against or placed upon by other devices or structures in the immediate environment. Additionally, the outer channel of the tubing of this embodiment of the present invention may be closed to or sealed to the inner channel at each end to prevent air movement and heat loss by convection.

BRIEF DESCRIPTION OF THE DRAWINGS

For a more complete understanding of the invention reference should be made to the drawings wherein:

FIG. 1 is a partial cross-sectional view of a first embodiment of the insulated I.V. tubing of the present invention;

FIG. 2 is an end view of the embodiment depicted in FIG. 1;

FIG. 3 is a partial cross-sectional and longitudinal view of a second embodiment of the present invention showing a double walled tube assembly;

FIG. 4 is an end view of the embodiment depicted in FIG. 3.

DESCRIPTION OF PREFERRED EMBODIMENTS

One embodiment of the present invention comprises a single I.V. tube having insulation, or heat reflective or heat resistant material applied on the outer surface, on the inner surface, or having such material blended into the I.V. tube material before or during formation of the tube. The tubing may be any known material which is suitable for such use and may be a naturally occurring or synthetically produced material.

The insulative material may be any known applicable insulative material and may be a gas, a liquid, or a solid. Alternatively, the insulation may consist of air or gas bubbles or substantially void, vacuum spaces in the tubing material. The use of a metallic film or a mylar film applied to the outer surface of the tube is particularly advantageous.

Representative examples of suitable plastic materials that can be used to provide an opaque or a transparent insulated tubing includes a variety of thermoplastic materials. Representative examples of suitable polymeric materials that can be used include polyethylene, polypropylene, polyurethane, polyvinyl chloride, silicone, Mylar, and the like. The insulated I.V. tubing material can be manufactured by known methods including extruding and other molding processes.

The shape of the insulated tubing can be of a standard rounded form or may be of rectangular form, or other geometric shape which is circular or cylindrical, square, hexagon, octagon, or polygon to provide an alternate three dimensional exterior.

One embodiment of the present invention includes medical solution or I.V. tubing manufactured of a polymeric material having good flexibility and comprising a heat resistant, insulative polymer.

Another embodiment of the present invention includes a polymeric tubing useful for medical applications comprising an inner layer comprising a polymeric material selected from the group consisting of polypropylene, ethylene propylene copolymer, modified ethylene propylene copolymer and the like; an outer layer, bonded to an outer surface of the inner layer and comprising a polymeric material which is insulative, heat reflective or heat resistant.

Advantageously the insulation is provided by a material attached to or blended within the I.V. tubing. In one embodiment the insulation material is urethane or polyisocyanurate. In another embodiment the insulation material is of fiberglass. While other insulation materials and combinations may be used in practicing this invention, it is believed that fiberglass provides one of the best cost-to-performance ratios. This particular material also provides good thermal insulation performance or efficiency. Even though the foregoing are the preferred materials, there are other materials and combinations which may be utilized in practicing this invention, including, but not limited to, the following:
(a) flexible fiberglass combined with flexible urethane;
(b) urethane combined with flexible ceramic fiber material;
(c) flexible mineral fiber material combined with flexible ceramic fiber material; and
(d) glass combined with flexible ceramic fiber material.

Another embodiment of the present invention is directed a coextruded, tri-layered medical tubing. The outer layer of the tubing is flexible PVC made with trioctyl trimellitate plasticizer (TOTM). The middle layer is comprised of EVA, and the inner layer of LDPE. The TOTM-based PVC, developed for blood contact applications, has exhibited exceptional bond strength with the EVA resin middle layer, thereby eliminating any separation problems previously encountered. This combination of materials maintains the structural integrity of the layer tubing construction even after a sterilization cycle.

The respective thickness of each layer of tubing can be controlled by the extrusion tooling utilized which results in concentric, uniform thickness and characteristics necessary for the high performance demanded by medical applications.

Another embodiment of the present invention provides an improved coextruded medical tubing that does not include PVC and materials for making same. The material of the present invention provides characteristics that are desirable in the medical industry and therefore can be used to make medical tubing for use in, for example, or blood donor tubes. At the same time, the present invention provides a non-PVC material.

The present invention provides a non-PVC coextruded medical grade tubing comprising: an outer layer comprising a blend of polypropylene copolymer and styrene-ethylene-butylene-styrene copolymer; an intermediate layer; and a core layer comprising a blend of polyamide and ethylene-vinyl acetate.

In one embodiment the polyamide component comprises at least two separate grades of polyamide. The resultant tubing is RF sealable, or heat sealable, to an olefinic surface. Such a tubing eliminates the concerns that have been raised with respect to a DEHP plasticized polyvinyl chloride material.

In one embodiment, the intermediate layer comprises a blend of polyester, polypropylene copolymer, styrene-ethylene-butylene-styrene copolymer, and ethylenevinyl acetate. Preferably, the tie layer is a blend comprising: approximately 30 to about 60% by weight copolyester; approximately 0 to about 20% by weight polypropylene copolymer; approximately 30 to about by weight styrene-ethylene-butylene-styrene copolymer; and approximately 0 to about 30% by weight ethylene vinyl acetate.

In one embodiment, the outer layer of the tube comprises approximately 40 to about 99% by weight polypropylene copolymer and approximately 1 to about 60% by weight styrene-ethylene-butylene-styrene copolymer.

An advantage of the present invention is that it can provide a non-PVC radio frequency active material. The material is RF sealable to olefinic materials such as polyethylene, polypropylene copolymer, and styrene-ethylene-butylene-styrene copolymer.

A further advantage of the present invention is that the material is flexible (has a low modulus), is optically clear and blush resistant, has excellent inter laminar strength, good compatibility, and is clampable.

Polyvinyl chloride (PVC) based tubing and tubing assemblies are used in numerous medical products. However, PVC is viewed as hazardous to both the environment and to personal health. Incineration of PVC results in the release of hydrochloric acid (HCl), and PVC is viewed as a major contributor to HCl in incinerator flue gases. Also, PVC is suspected of contributing to polychlorinated dibenzodioxin and furan toxins formed during incineration. Levels of these toxins are up to three times greater in medical infectious waste as compared to municipal waste streams. In addition to incineration concerns, exposure to di-2-ethylhexyl phthalate (DEHP), a common plasticizer used with PVC, may present a number of health related concerns, including reduced blood platelet efficacy and potential links to liver cancer. PVC is also known to adsorb certain drugs, such as nitroglycerin and insulin. This can reduce the efficiency and accuracy of drug delivery.

Despite these concerns, PVC-based tubing and tubing assemblies, continue to be the material of choice in scientific and medical applications. The continued use of PVC materials is due, at least in part, to PVC's attractive qualities, including flexibility; toughness; resistance to UV light, gamma irradiation, solvents, cuts, scratches, and acids;

clarity or opaqueness as required; and low cost. In addition, PVC's characteristics can be modified through the addition of various additives, such as plasticizers, colorants, and the like.

Thermoplastic polymers other than PVC have been used to form single-layer tubing and tubing assemblies. For example, low-density polyethylene, high density polyethylene, polypropylene, ethylene vinyl acetate, polybutylene, and the like have all been used to form single-layer tubing and tubing assemblies. Several commercial offerings of non-PVC medical tubing sets are available on the market, such as polybutadiene-based material which is translucent and kinks easily, of a 3-layer type construction, with the outer layer consisting of plasticized PVC; an intravenous (IV) tubing which is a two layered tubing with the outer layer an EVA copolymer and the inner layer made of polyethylene. However, none of these polymer materials has the advantageous characteristics needed to serve as an environmentally compatible replacement for PVC-based materials. In addition, some of the above noted materials are polyolefins or their copolymers. Polyolefins generally have low surface energies which makes them difficult to bond with conventional adhesives or solvents.

One embodiment of the present invention provides a polymer blend which is environmentally compatible, while still being surprisingly tough considering its high flexibility and kink resistance. Tubes and sheets made from this blend have good transparency, are solvent, UV light, and gamma irradiation resistant, and can be made for an acceptable cost.

In one aspect, the invention provides a tube comprising a polymeric material that is a blend of a thermoplastic ionomer, which particularly imparts the properties of strength and a good surface finish to the blend, and a non-ionic thermoplastic polymer, which particularly imparts the properties of flexibility and kink/rekink resistance to the blend.

In tubes of the present invention, suitable thermoplastic ionomers includes ionic polymers consisting of an organic backbone and having pendant acidic groups (e.g., carboxylic acid groups, sulfonic acid groups, etc.) which are neutralized either partially or completely with metal or quaternary ammonium ions. Advantageously, the thermoplastic ionomer will be composed of an ionomeric copolymer selected from the group consisting of copolymer of ethylene and acrylic acid-metal cation neutralized salt, or of ethylene and methacrylic acid-metal cation neutralized salt. Two or more different thermoplastic ionomers may be used in the blends of the present invention. Examples of preferred thermoplastic ionomers include ionomeric ethylene-methacrylic acid copolymer with zinc (EMAZ) or sodium (EMAS) neutralization. Ethylene/acrylate/acrylic acid copolymer with zinc neutralization, are also considered suitable.

In tubes of the present invention, the non-ionic thermoplastic polymer is advantageously selected from the group consisting of polymers of olefin monomers, copolymers of olefin monomers, substituted olefin monomers, and the like. Preferably the non-ionic thermoplastic polymer within the blend is selected from the group consisting of polymers of a $C_2$ to $C_4$ mono-unsaturated alkene; copolymers of a majority of a $C_2$ to $C_4$ mono-unsaturated alkene with a minority of a substituted olefin monomer such as $C_4$ to $C_{14}$ mono-unsaturated alkene; or copolymers of a majority of a $C_2$ to $C_4$ mono-unsaturated alkene with a minority of a substituted C2 to C6 mono-unsaturated alkene having a substituent such as carboxylic acid ester groups. Examples of the first class include polyethylene (PE), polypropylene (PP), and copolymers of ethylene with butene (EB) or propylene with butene (PB). Examples of the second class include copolymers of ethylene with octene (EO) or propylene with octene (PO). Examples of the third class include copolymers of olefins such as ethylene or propylene with substituted olefins such as vinyl acetate (EVA or PVA). Other examples of the third class include copolymers of ethylene and n-butyl acrylate, and copolymers of ethylene and ethyl acrylate. Two or more different non-ionic thermoplastic polymers may be used in the blends of the present invention.

Some specific materials which are considered suitable include ethylene/butene copolymer; ethylene/alpha-olefin copolymer; ethylene/octene copolymer; ethylene/acetate copolymer, and the like.

The tubing of the present invention is flexible, tough and abrasion resistant. The tubing also possesses a remarkable resistance to kinking during bending and rekinking in a location that has already been kinked when compared to alternatives of similar cost. Embodiments which are chlorine-free include embodiments which do not release harmful chemicals such as hydrogen chloride to the atmosphere when they are burned or otherwise degraded. The tubing of the present invention is also safe and effective for use in medical applications, and preferably for that application contain no plasticizers or other leachable or exudable ingredients which could contaminate pharmaceutical fluids. In particular, at least the fluid contacting surfaces of the tubing contain no phthalate or citrate esters or other plasticizers or additives which are capable of leaching into pharmaceutical fluids. The tubing, also preferably avoids absorption of solvents, drugs, pharmaceutical agents and other materials which come in contact with them. This characteristic is especially desirable when the tube is used in a medical product. In this application, the tubing displays minimal or no absorption of drug, pharmaceutical carrier or other pharmaceutical liquid. Optionally, the tubing can be composed of thermoplastic polymers which will make the layers resistant to acid, solvent, UV light, and gamma sterilization, and will render the tube clear or opaque or colored.

The present invention includes I.V. tubing formed from a radial block copolymer mixture which is composed of from about 10–90% by weight of a butadiene-styrene radial block copolymer having a butadiene content in the range of about 85–60% by weight and a styrene content in the range of about 15–40% by weight, from about 90–10% by weight of a butadiene-styrene radial block copolymer having differing butadiene contents in the range of about 85–60% by weight and a styrene content in the range of about 15–40% by weight and 5–75% by weight of the radial block copolymer of certain polymeric or copolymeric materials such as acrylics, thermoplastic epoxides, styrene acrylonitrile, polycarbonates, polybutenes and polyisobutylenes, polyesters, polyolefins, polystyrenes, polyvinylchloride and olefin/P.V.C. copolymers, polyether and polyester urethane polymers and methacrylate-styrene-butadiene copolymers and mixtures thereof. Of the foregoing those preferred are thermoplastic polyether urethane polymers, methyl methacrylate-styrene-butadiene copolymers, methyl methacrylate-acrylonitrile-styrene-butadiene copolymers and thermoplastic polyester urethane polymers, and mixtures thereof. In a preferred composition, one of the radial block copolymers has a butadiene content of about 70% by weight and a styrene content of 30% by weight and the other butadiene-styrene copolymer has a butadiene content of about 60% by weight and a styrene content of about 40% by weight with the copolymer having the 70:30 butadiene-styrene ratio present in an amount in the range of about 90–45% by weight with the polymer having the 60:40 butadiene-styrene ratio present in the range of about 10–55% by weight with a 75 to 25% ratio preferable.

In one embodiment of the present invention the multilayered tubing of the possesses physical characteristics much like those of polyvinyl chloride medical tubing. In addition, the multilayered tubing is environmentally safe and avoids medical, pharmaceutical and health-related drawbacks of polyvinyl chloride tubing as mentioned above.

The wall of the multilayered tubing is made of multiple layers of thermoplastic polymer. The multiple layers provide composite characteristics so that the wall mimics and in preferred embodiments is better than PVC for many uses. A minimum number of layers for the wall is two: an outer surface layer and an inner layer. A majority of the wall thickness is preferably provided by the inner layer. This layer acts as the core of the wall to provide such characteristics as flexibility, and resilience to the multilayered tubing. Other layers such as the outside surface layer and, in a wall configuration of three or more layers, the inside surface layer, provide toughness, tensile strength and abrasion-resistance to the tubing. These layers are generally thinner than the layer or layers making up the flexible core of the wall so that their physical characteristics do not dominate the composite characteristics of the multilayered tubing.

Toughness and resistance toward abrasion and cuts as well as high flexibility are physical characteristics that are important for medical tubing. The medical tubing preferably can survive the long term abrasion forces of such medical instruments as infusion pumps and friction fittings. It also preferably has a high flexibility so that it can be formed into tight loops and bends which are important for catheter formation and delivery tube service.

Tough, abrasion resistant thermoplastic polymers typically are not flexible enough for use in such medical tubing. Highly flexible thermoplastic polymers typically are not tough enough for use in such medical tubing.

According to an embodiment of the present invention, a multilayered tubing is provided which has been developed which has a flexibility, a kink/rekink resistance, a tensile strength, a toughness and an abrasion resistance mimicking or exceeding PVC. The multilayered tubing has a wall composed of a core of at least one inner layer of at least one flexible chlorine-free first thermoplastic polymer and an outside surface layer of at least one tough, chlorine-free second thermoplastic polymer. When the wall contains three or more layers, there is also an inside surface layer of at least one tough, chlorine-free third thermoplastic polymer. One or more optional layers of at least the first, second or third thermoplastic polymer can also be included in the wall. Although it is preferred to use one thermoplastic polymer for a wall layer, such layers may also be composed of physical mixtures of thermoplastic polymers. To achieve the foregoing characteristics, the multilayered tubing incorporates at least the following parameters a through c and preferably the remaining parameters as well:

(a) The first thermoplastic polymer has a flexibility mimicing or greater than that of polyvinyl chloride medical tubing. More specifically, the first thermoplastic polymer has a flexibility substantially needed to achieve a flex function for the tubing which ranges from a capability to flex through body part lumen to a capability to be formed into an acute curve without creating a cross-sectional crease which would stop the flow of fluid or air passing through the tubing bore. Preferably the flexibility of the first thermoplastic polymer is measured by its Young's modulus which in especially preferred embodiments is within a range of about 2 to about 60 MPa (megaPascals).

(b) The second thermoplastic polymer has a Young's modulus that is not more than about fifteen times, preferably from about equal to, up to no greater than, about fifteen times, more preferably within a range of greater than, up to about fifteen times, the Young's modulus of the first thermoplastic polymer. Especially preferably, the Young's modulus of the second thermoplastic polymer is up to no more than about seven times, most preferably up to no more than about three times, the Young's modulus of the first thermoplastic polymer. Preferred embodiments have a Young's modulus of the second thermoplastic polymer within a range of from about 15 to 300 MPa, more preferably within a range of from about 20 to 150 MPa, more especially 20 to 45 MPa.

(c) The core of the tubing wall provides at least a slight majority of the wall thickness relative to any other single layer. The core includes the inner layer of the wall as well as any other layers composed at least of the first thermoplastic polymer. More specifically, the thickness ratio of the wall layers incorporating first thermoplastic polymer to the wall layers incorporating second, third and additional thermoplastic polymer is about 1:1 to about 30:1, preferably from about 1:1 to about 10:1, more preferably from about 1:1 to about 5:1. This parameter allows the flexibility of the wall core to dominate the composite characteristics of the multilayered tubing.

(d) The multilayered tubing preferably exhibits a kink/rekink resistance that mimics or is greater than that of polyvinyl chloride medical tubing. Examples of such medical tubing include those given in foregoing paragraph a. Preferably, the kink/rekink resistance of the tubing is in a range of from about 1.8 or greater, more preferably from about 2.0, especially 2.2 or greater as measured by the kink-o-meter test described in the following examples section. Although relation to the kink/rekink of medical PVC tubing is referenced, the invention includes application of the multilayer tubing to non-medical tubing uses needing a similar resistance function.

(e) In addition to the flexibility of the first thermoplastic polymer and the core of the tubing wall, the multilayered tubing itself preferably exhibits a flexibility that mimics or is greater than that of polyvinyl chloride medical tubing. Examples of such medical tubing include those given in foregoing paragraph a. More preferably, the multilayered tubing has a Young's modulus within a range of about 15 to about 60 MPa. Although relation to the kink/rekink of PVC medical tubing is referenced, the invention includes application of the multilayer tubing to non-medical tubing uses needing a similar resistance function.

(f) The multilayered tubing preferably exhibits a tensile strength that is lower than that of polyvinyl chloride medical tubing but not so low as to deform to constrict the bore when pulled at both tubing ends by medical personnel. To compensate for lower tensile strength, the tubing can be made with thicker walls. Tubing samples have been tested with the pinch and roller clamps used in standard polyvinyl chloride IV sets and by nurses and found to be of sufficient strength for typical medical use.

(g) The outside surface layer of the tubing wall and in preferred embodiments, the multilayered tubing itself preferably exhibits an abrasion resistance that mimics or is greater than that of polyvinyl chloride medical tubing. Examples of such medical tubing include those given in foregoing paragraph a. More specifically, the outside surface layer of the tubing wall and preferably, the multilayered tubing itself exhibits an outside surface abrasion resistance within an abrasive index range of about 100 or greater as measured by ASTM test D1630-83, standard test method for rubber property-abrasion resistance (NBS abrader). Although relation to the abrasion resistance of PVC medical tubing is referenced, the invention includes application of the multilayer tubing to non-medical tubing uses needing a similar resistance function.

(h) The multilayered tubing preferably exhibits essentially complete resiliency and essentially no wall failure throughout at least a 45 hour period of a simple Clamp Test as described in the Tubing Clamp Test in the Examples. Such a resiliency includes an ability of the tubing wall to be completely collapsed without suffering permanent distortion. The wall should return to its original state to show essentially complete resiliency. It should not crack or exhibit signs of stress weakening to show essentially no wall failure.

The kink/rekink resistance of the multilayered tubing is an important physical characteristic. Resistance to kinking is the ability of the tubing to resist the tendency, upon bending, to form a cross-sectional crease in the tubing wall. Such a crease could completely or partially shut off or occlude fluid flow in the bore of the tubing. The resistance toward rekink is the ability of the tubing to resist a tendency to reform a crease in the wall after having been kinked. The kink/rekink resistance of tubing can be tested with a "Kink-O-Meter".

Generally, the multilayered tubing of the invention will exhibit a kink/rekink characteristic between that of the individual layers of the wall as would be expected. However, preferred embodiments of the multilayered tubing have an unexpected kink/rekink resistance. These embodiments exhibit a kink/rekink resistance which is significantly better than that of the individual layers. For example, a multilayered tubing made of an inner layer of a copolymer of ethylene and butene and an outside surface layer of an ionomeric copolymer of ethylene and methacrylic acid with zinc or sodium ions displays surprising kink/rekink resistance characteristics relative to single layer tubings of the same dimension and the individual polymers.

In a further embodiment the first thermoplastic polymer is used to form the inner layer serving as the core of the tubing wall. It includes any soft conformable thermoplastic polymer having the characteristics, flexibility and preferably the Young's modulus described above. Preferred thermoplastics include polymers of a $C_2$ to $C_4$ mono-unsaturated alkene, copolymers of a majority of a $C_2$ to $C_4$ mono-unsaturated alkene with a minority of a substituted olefin monomer such as $C_4$ to $C_{14}$ mono-unsaturated alkene or a $C_8$ to $C_{14}$ aryl alkene, and copolymers of a majority of a $C_2$ to $C_4$ mono-unsaturated alkene with a minority of a substituted $C_2$ to $C_6$ mono-unsaturated alkene having a substituent such as $C_1$ to $C_6$ alkoxy carbonyl, carboxylic acid, carboxamide and carboxylic ester groups. Examples include copolymers of olefins such as ethylene and propylene with substituted olefins such as vinyl acetate (EVA or PVA), N-methyl acrylamide (EAM or PAM), acrylic acid (EAA or PAA), methacrylic acid (EMA and PMA), EMA or PMA ionomers (EMAZ or PMAZ with zinc; EMAS or PMAS with sodium) and acrylate and methacrylic esters having $C_1$ to $C_6$ alkyl groups. In the case of the copolymer of PVA, the acetate can be partially or wholly hydrolyzed to yield polyvinyl alcohol (PVO). Examples as well include ethylene or propylene copolymers of all hydrocarbon substituted olefins such as ethylene or propylene and styrene (ES or PS), ethylene or propylene and butene (EB or PB) and ethylene or propylene and octene (EO or PO). Particular examples include copolymers of ethylene and vinyl acetate (EVA), ethylene and butene (EB), ethylene and n-butyl acrylate (EBA), and ethylene and ethyl acrylate (EEA).

Generally, as the amount of substituted olefin monomer or alkyl or aryl olefin monomer is increased in such an olefin copolymer, the Young's modulus of the copolymer will decrease. Consequently, the ratio of majority olefin monomer to minority substituted olefin monomer in the copolymer will be selected so that the copolymer will have the appropriate Young's modulus as described above. Preferably, this amount is from about 2% to about 50%, especially preferably about 10% to about 40% on a weight basis.

The second and third thermoplastic polymers include any tough, abrasion resistant thermoplastic polymer having the characteristics and the high Young's modulus described above. The second and third thermoplastic polymers can have any suitable backbone structure such as cross-linking, pseudo-cross-linking, backbone branching, randomization, grafting, ionomeric linking, a combination of crystalline and amorphous domains, hydrogen bonding, and backbone structures that restrict the degrees of three dimensional movement of the backbone. By selecting an appropriate backbone character, the degree of substitution on the monomers and the amount of minor monomer present, a tensile strength, Young's modulus and abrasion resistance suitable for the tubing can be obtained. Generally the second and third thermoplastic polymers have the same characteristics but are not necessarily of the same chemical structure. Preferably, the second and third thermoplastic polymers include polyolefins, cross-linked polyolefins, olefin-substituted olefin copolymers as well as polyurethanes, polyethers, and polyesters.

The olefinic monomers used alone or in combination to form the polyolefins can be selected from aliphatic and aromatic olefins of two to fourteen carbons such as ethylene, propylene, butene, octene and styrene. Preferred polymers and copolymers of such olefins include polyethylene, polypropylene, copolymers of ethylene and butene (EB) and copolymers of ethylene and styrene (ES). In copolymers of olefins, the minor olefin monomer (C4 to C14) preferably is present in a range of from about 2% to about 20% on a weight basis.

When a copolymer is used for the second or third thermoplastic polymer, it can also be formed of a $C_2$ to $C_4$ olefin monomer and a substituted olefinic monomer selected from $C_2$ to $C_6$ mono-unsaturated olefins having such substituents as oxyalkanoyl, carboxyl, carboxamido and other similar polar groups. Examples include acrylic acid, methacrylic acid, acrylamide and similar hydrogen bonding or cross-linkable olefins.

The backbone structures degree of substitution and amount of minor monomer present is mentioned above for the second and third thermoplastic polymers will be selected so as to preserve the thermoplastic character of the polymer and to provide the degree of abrasion resistance, toughness and stiffness meeting the Young's modulus requirement described above. Moreover, the thermoplastic olefin copolymers are selected for use as second and third thermoplastic polymers according to the guidelines given above for variation of Young's modulus. Preferred olefin copolymers include a majority of $C_2$ to $C_4$ olefin monomer and a minority of substituted olefin monomer. Preferably, the amount of minority monomer present is from about 2% to about 40%, preferably about 2% to about 20% on a weight basis. The higher amount of minority monomer in such copolymer makes the copolymer stiffer and tougher.

In preferred embodiments, the first, second and third chlorine-free thermoplastic polymers are all olefinic polymers. Examples of preferred first thermoplastic olefinic polymers include ethylene-vinyl acetate copolymers (EVA), ethylene alkyl acrylate copolymers such as ethylene n-butyl acrylate copolymers (EBA), ethylene-butene copolymers (EB), ethylene-octene copolymers (EO) and combinations thereof. Nonlimiting examples of second and third thermoplastic olefinic polymers include ethylene acrylic acid copolymer and ionomeric ethylene-methacrylic acid copolymer with zinc or sodium.

The first, second and third thermoplastic polymers may also constitute olefin copolymers of the same two monomers but with differing ratios of those monomers. That differing ratio changes the modulus value of the resulting copolymer and hence makes the copolymer a first, second and third thermoplastic polymer. For example, the first, second and third thermoplastic polymers can all be obtained from EVA and EBA copolymers by altering the percent by weight content of vinyl acetate (VA) and n-butyl acrylate (n-BA) monomers, respectively, in those EVA and EBA copolymers. EVA and EBA copolymers with relatively high VA and n-BA contents provide low Young's modulus materials suitable for use in the inner layer of the multilayered tubing. On the other hand, EVA and EBA copolymers with relatively low VA and n-BA contents provide high Young's modulus materials suitable for use in the outside surface layer and, for a tubing of three or more layers, the inside surface layer. For example, when an EBA copolymer composes the inner layer and the outside and inside surface layers, its n-BA content is preferably from about 15 to 30% for the inner layer, and preferably from about 1% to about 20%, more preferably from about 1% to about 15%, and most preferably from about 2% to about 10% for the surface layers, the percentage being on a molar basis. In another example the inner layer of a three layer wall is an EVA copolymer with a VA content of from about 15% to about 40% VA, while the outside and inside surface layers are EVA copolymer with a VA content of from about 1% to about 20% VA on a weight basis. Alternatively, the outside surface layer of that wall can be an EVA copolymer with a VA content of from about 1% to about 20% VA, while the inside surface layer of that wall can be an EVA copolymer with a VA content of from about 15% to about 40% percent VA on a weight basis.

The diameter of the multilayered tubing and its wall thickness will vary depending upon the intended use, and thus, can readily be selected by those skilled in the art.

As generally explained above, the layer or layers forming the flexible core of the tubing wall may be slightly to significantly larger in thickness than any other single tough layer of the wall. This factor allows the core characteristics of the wall to dominate the characteristics of the tubing. In a preferred embodiment, the outside surface layer and for a tubing of three or more layers, the inside surface layer, are thin protective coverings for the core of the wall. In particular, the increased hardness and toughness of the second and third thermoplastic polymers allows them to be coextruded as substantially thinner layers, and yet still provide adequate tensile strength to the tubing and adequate protection for the flexible core of first thermoplastic polymer. Generally, any ratio of inner layer or layers to outside surface layer, and for a wall configuration of three layers or more, any ratio of inner layer or layers to outside and inside surface layers, will suffice as long as it provides adequate tensile strength to the tubing and adequate protection of the wall core of first thermoplastic polymer. Numeric parameters are as given above in paragraph c of the parameters section.

In a preferred embodiment, when using the preferred EVA or EB and EMAZ or EMAS ionomeric copolymers to form a two-layer or three-layer tubing according to the present invention, the inner layer is preferably from about 200.mu. to about 1200.mu., more preferably from about 200.mu. to about 1000.mu., and most preferably from about 200.mu. to about 600.mu. thick, while the outside and inside surface layers are preferably from about 10.mu. to about 800.mu., more preferably from about 50.mu. to about 600.mu., and most preferably from about 50.mu. to about 200.mu. thick.

The stiffness/flexibility of a given thermoplastic polymer is conveniently measured and expressed in terms of the Young's modulus, as reported in megapascals (MPa), for the polymer. A polymer with a low Young's modulus (e.g., from about 2 MPa to about 60 MPa) is soft and flexible while a polymer with higher Young's modulus values (e.g., from about 15 MPa to about 300 MPa) is relatively stiff and inflexible. The low Young's modulus polymers also tend to be more easily cut or physically abraded and serve as the first thermoplastic polymer. Conversely, the high Young's modulus polymers present a relatively hard, tough (i.e., cut and scratch-resistant) surface and serve as the second and/or third thermoplastic polymers.

The measurement of Young's modulus follows the procedure outlined by the reference guide for "Instron Series IX Automated Materials Testing System" Version 5, Instron Company, Canton, Mass.; pp 13–19 to 13–27; Issue B, November, 1990 incorporated herein by reference. The functional and numeric parameters for abrasive-resistance and flexibility of the first, second and third thermoplastic polymers used in the wall of the multilayered tubing are related to, and in preferred embodiments, are indicated by the Young's modulus of these polymers.

Referring now to the drawings, FIGS. 1 and 2 is a view of the first embodiment of the insulated I.V. tubing of the present invention, 10. As shown in FIG. 1 tube 10 has an outer surface 11, inner surface 12 and manufactured of material 15. Insulation material 13 may be on the interior surface, exterior surface (as depicted in FIG. 1) or interspersed within the material 15. Optionally, insulating material 13 may be applied to tube 10 by apparatus 14.

In one embodiment, shown in FIGS. 3 and 4, the tube may have the insulation or covering adhered to an inner tubular channel which may be attached to an outer tubular channel 32 by means of central support structures 35. The optional central support structures are placed between the openings of inner and outer tubular channels 35, 32. A separating, insulating space 33 is maintained between the inner tubular channel 35 and the outer tubular channel 32. As shown in FIGS. 3 and 4 tube 30 has an outer surface 31, an inner surface 33 and is comprised of material 32. Insulating space 34 is present between tube 35 and tube 32. Tube 35 has outer surface 36 and inner surface 37 and may be manufactured of material similar to outer tube 32 or dissimilar therefrom.

Ancillary support structures may be required to maintain centering of the inner tubular channel within the outer tubular channel. The number and placement of the ancillary support structures can be varied about the circumferences of the inner and outer tubular channels. It may not be necessary to have any such support structures, or only one, two or three appropriately placed ancillary support structures may maintain centering of the inner tubular channel throughout the length of the insulation device. The support structures can be of the same material as the inner and outer channels and can be formed integrally therewith.

The overall length of the insulated tubing can provide coverage for the length of the patient's I.V. administration tubing and can come as one, two or more sections. The I.V. drip chamber and flow rate controller of the I.V. administration set (not shown) can be excluded from the insulated tubing by attaching one sectional length of the insulated tubing between the I.V. reservoir bag and the drip chamber. Further, another sectional length of the insulated tubing can be applied between the drip chamber and patient's anatomic I.V. site. Alternatively, the insulated tubing can incorporate the drip chamber by increasing the diameters (not shown) of the inner and outer tubular channels to accommodate the short sectional length of any larger tubular drip chambers. The flow rate controller of the I.V. administration set is usually of a thumb-wheel roller clamp type that can be partially or completely placed inside the inner tubular channel providing insulation while permitting access to adjust I.V. fluid flow rate.

The wall thickness of the inner and outer tubular channels can be adjusted to permit various degrees of rigidity to allow flexibility of the insulated tubing during patient use to permit bending about the patient's arms or other operating room structures and thereby avoiding kinking and undue stress to the inserted I.V. tubing. All components can be made of transparent plastic-like material to permit visualization and easy detection of air bubbles in the fluid of the I.V. tubing when in patient use.

An adhesive tape-like or bonding material can be applied to partially or completely seal the sections of tubing together and may be applied to secure the I.V. tubing in place. An insulating space may be provided within the I.V. tubing bounded by the surfaces of the two tubes.

In all embodiments, the structure of the insulated tubing is formed of commercially available materials and is therefore uncomplicated and inexpensive to manufacture. It is small, lightweight, and portable and provides predictable insulation of I.V. administration tubing carrying warmed I.V. fluids to the patient in cooler environments. It is free of any attachment to a remote energy source.

When present, the internal insulation space may be a vacuum or may be filled with air or other light-weight insulation material. The actual physical dimension of separation between the inner channel and the outer channel can be varied to achieve adequate insulation and minimum bulk.

FIG. 3 is a schematic cross-section of a two layer tubing made in accordance with the invention. FIG. 3 shows a two layer tubing 30 in accordance with the invention. The inner layer may be an ethylene propylene copolymer (EPC) or modified EPC. This copolymer advantageously has an ethylene content of about 3.8%. A suitable modified EPC is one containing a blend of ethylene propylene copolymer and styrene ethylene butylene styrene copolymer. Polyallomers may also be used, such as ethylene propylene block copolymer, having a melt flow index of about 12.

The outer layer may be ethylene propylene copolymer, or a flexible copolyester, more preferably a copolymer of polyether and polyethylene terephthalate. These particular copolyesters are characterized by inherent viscosities ranging from 1.05 to 1.28, and by the use of 1,4 cyclohexane dimethanol, 1,4 cyclohexane dicarboxylic acid, and polytetramethylene glycol ether as reactants in producing the flexible copolyester. Polypropylene may also be used in outer layer 26. The materials of outer layer 26 are especially chosen for their heat resistance and insulation ability.

The tubing may be formed by conventional coextrusion means and may optionally be cross-linked by radiation techniques well known in the art. Alternatively, a chemical cross-linking agent may be introduced to the resin melt of any or all of the layer discussed above prior to extrusion to effect the cross-linking of the tubing.

Another embodiment of the present invention relates to an elongate double-walled tube assembly, such as a concentric double-walled tube assembly, of thermoplastic resin, which tube is capable of passing a fluid and a method of continuously manufacturing such an elongate double-walled tube assembly with dimensional accuracy and reproducibility through extrusion molding, using an extrusion molding machine having a cross-head die, and a sizing die device.

According to the disclosed manufacturing method, (a) two extrusion molding machines are used, (b) an inner tube and connecting ribs are separately formed by the first extrusion molding machine, (c) thereafter, the inner tube and the connecting ribs are welded and extruded together, (d) an outer tube is extruded by the second extrusion molding machine and is simultaneously joined to the unitary body of the inner tube and connecting ribs by a crosshead associated with the second extrusion molding machine, (e) so that a double-walled tube assembly of an integral structure is produced in which the outer tube and the connecting ribs are separable from each other and the connecting ribs and the inner tube are separable from each other.

With the known manufacturing method, the inner tube and the connecting ribs are separately extruded as a unitary body by the first extrusion molding machine. Thereafter the outer tube which is extruded by the second extrusion molding machine is melted and integrally joined to the inner tube and the connecting ribs by the crosshead for thereby producing a double-walled tube assembly of thermoplastic resin. Therefore, when the ribs are brought into contact with the melted outer tube, the ribs are deformed because of the high temperature of the outer tube. Moreover, at the time the inner tube, the ribs, and the softened outer tube are cooled and solidified after they have been extruded from the crossdie, the outer tube shrinks radially inwardly toward the inner tube. As a consequence, double-walled tube assemblies with outer tubes of high dimensional accuracy cannot be manufactured by the conventional method.

With the aforesaid conventional method, since the inner tube and the outer tube are independently extruded and then joined to each other, it would substantially be difficult to sufficiently reduce the width of the ribs and hence ribs of large width should be employed for preventing the ribs from being deformed at high temperature. Thus, the outer and inner tubes of the prior double-walled tube assembly are integrally joined to each other by the ribs of large width. The double-walled tube assembly is highly rigid, but not flexible enough to be freely curved or bent for use.

As shown in FIGS. 3 and 4, a double-walled tube assembly according to the present invention may comprise an elongate inner tube molded of thermoplastic resin such as nylon (especially, nylon 12, nylon 66, nylon 6, or the like), polyester, polyethylene, polypropylene, or the like, and an outer tube of larger diameter molded of the same thermoplastic resin as that of the inner tube, the outer tube may have a plurality of angularly spaced ridges or ribs projecting from the inner wall surface thereof toward the central axis thereof. The height of each of the ribs from the inner wall surface of the outer tube to the distal inner end of the rib remains constant in the longitudinal direction of the outer tube. The distal inner ends of the ribs are fused to the outer circumferential surface of the inner tube over the entire length of the inner and outer tubes, which are disposed substantially concentrically with each other.

Preferably two to four ribs project from the inner wall surface of the outer tube toward the central axis thereof. The double-walled tube assembly of the present invention is not limited to particular dimensions and sizes.

The double-walled tube assembly can be molded by an extrusion molding machine having a cross-head die, and a sizing die in common.

The extrusion molding machine used for continuously manufacturing the double-walled tube assembly has a resin passage and a discharge port capable of extruding a melted mass of thermoplastic resin supplied by a feed screw as an elongate outer tube having a plurality of ridges or ribs of constant height projecting toward the center of the outer tube and extending the entire length of the inner wall surface of the outer tube.

The extrusion molding machine also has a cross-head die having an inner tube insertion passage capable of feeding an elongate inner tube that has separately been extrusion-molded of thermoplastic resin, centrally through the resin passage and the discharge port, which are defined in the cross-head die.

According to the manufacturing method of one embodiment of the present invention, the elongate inner tube is continuously fed through the cross-head die, while the melted mass of thermoplastic resin flowing from the resin passage is being discharged from the discharge port to extrude the outer tube concentrically around the inner tube.

The outer tube immediately after it is extruded from the discharge port of the cross-head die is not in direct contact with the outer peripheral wall of the inner tube as it emerges centrally from the cross head die. It is preferable that the outer peripheral surface of the inner tube and the distal ends of the ribs of the outer tube be spaced from each other.

Both the inner tube and the melted outer tube discharged from the cross-head die are then fed to a sizing die device, the outer peripheral surface of the outer tube is cooled by ambient cooling air brought into contact therewith, changing the outer tube from the melted state to a stabler softened state. The outer tube is thus prevented from being excessively deformed due to its flowability.

The inner tube and the softened outer tube are continuously fed together into a sizing die. At the same time, the outer tube is cooled and solidified while its outer profile is being adjusted. Finally, a double-walled tube assembly with the inner tube and the outer tube is produced.

The sizing die device may be of any construction insofar as it can contract the softened outer tube extruded from the cross-head die toward the outer peripheral surface of the inner tube and also can cool and solidify the outer tube while adjusting its outer profile to shape.

The tubing of the present invention may be produced by a separately pre-molded inner tube that is fed to an extrusion molding machine having a cross-head die, and an outer tube having ribs is extruded around the inner tube by the cross-head die, and then the inner tube and the outer tube are supplied into a sizing die device.

EXAMPLE

It was proposed to use external I.V. fluid warmers to pre-warm all I.V. fluids to about 40.degree. C. and, to conserve heat energy, insulate the I.V. solution reservoir (bag or bottle) and use insulated I.V. tubing except for the drip chamber and roller clamp/injection-site area during patient use.

To determine if insulating the I.V. reservoir bag and administration tubing would be an effective technique to provide warmed I.V. fluids and for how long, the following tests were performed:

I. 500 mL plastic I.V. bags of 0.9% sodium chloride solution were warmed to 40.degree. C. and allowed to cool to an ambient temperature between 22.degree.–23.degree. C. Temperature curves for the decrease in temperature with time were measured about every 10 minutes within the I.V. bag with: 1) no insulation and 2) 5/8" bubble-wrap insulation, wrapped one thickness and taped in place.

II. 500 mL plastic I.V. bags were warmed to 40.degree. C. and the fluid contents emptied through a standard I.V. administration set at 30 and 60 mL/minute flow rates. The temperature of the fluid exiting the I.V. tubing was measured every 1.5 minutes with the I.V. bag and I.V. tubing having 1) no insulation and 2) insulated with 5/8" bubble-wrap, one thickness about all surfaces taped in place, drip chamber and roller-clamp areas excluded.

The standard I.V. administration set consisted of a non-vented drip chamber, 68" of 1/8" I.V. tubing, roller clamp, injection site, 4-way stopcock, 33" of 3/16 O.D. I.V. tubing and terminated with a 16 ga 2" I.V. cannula.

The results of the above tests are as follows:

I.1. Warmed I.V. Bag with no insulation—temperature decreased from 40.degree. C. to 32.8.degree. C. at 1 hour, 28.8.degree. C. at 2 hours, I.2. Warmed I.V. Bag with insulation—temperature decreased from 40.8.degree. C. to 36.8.degree. C. at 1 hour, 33.4.degree. C. at 2 hours.

II.1. Oulet temperatures with I.V. Bag and I.V. tubing (no insulation)

@ 30 mL/minute: temperature peaked at 35.5.degree. C. in 2 minutes, then almost linearly decreased to 31.degree. C. in 30 minutes.

@ 60 mL/minute: temperature peaked at 37.2.degree. C. in 2 minutes, then almost linearly decreased to 34.8.degree. C. in 17 minutes.

II.2. Outlet temperatures with Insulated I.V. Bag and I.V. tubing:

@ 30 mL/minute: temperature peaked at 37.0.degree. C. in 2 minutes, then almost linearly decreased to 33.4.degree. C. in 31 minutes.

@ 60 mL/minute: temperature peaked at 38.2.degree. C. in 2 minutes, then almost linearly decreased to 36.8.degree. C. in 18 minutes.

This study demonstrates that a pre-heated I.V. fluid( to about 40.degree. C.) container can be insulated and effectively administered through an insulated I.V. administration set at slow flow rates of 30 and 60 mL/minute, and maintain I.V. fluid temperature above 33.degree. C. and 36.degree. C., respectively. Faster I.V. fluid flow rates will almost certainly produce better results. In addition, the insulated pre-warmed I.V. fluid bag can remain in a warm state (above 33.degree. C.) for about two hours.

While the present invention has been described in accordance with the preferred embodiments of the various figures, it is understood that other similar embodiments may be used or modifications and additions may be made to the described embodiments for performing the same functions of the present invention without deviating therefrom. Therefore, the present invention should not be limited to any single embodiment but rather construed in breadth and scope in accordance with the recitation of the appended claims.

What is claimed is:

1. A tubing for transportation of intravenous fluids comprising:

(a) an inner layer comprising modified ethylene propylene copolymer; and (b) an outer layer of heat reflective or heat resistant insulation material consisting of a blend of copolyester and ethylene vinyl acetate copolymer bonded to a surface of the inner inner layer.

2. The tubing of claim 1 wherein the insulation material is substantially a solid.

3. A tubing for transportation of intravenous fluids comprising:
   (a) an inner layer comprising modified ethylene propylene copolymer; and
   (b) an outer layer of heat reflective or heat resistant insulation material bonded to a surface of the inner layer, which insulation material is polymeric and comprises at least one polymer selected from the group consisting of: polyethylene terephthalate and ethylene/vinyl acetate copolymer.

4. The tubing of claim 1 wherein the inner layer is synthetically produced material.

5. The polymeric tubing of claim 4 wherein the tubing is cross-linked.

6. The polymeric tubing of claim 5 wherein the tubing is cross-linked by irradiation.

* * * * *